(12) United States Patent
Roberts et al.

(10) Patent No.: US 9,192,731 B2
(45) Date of Patent: Nov. 24, 2015

(54) SAFETY DEVICE FOR A PRE-FILLED SYRINGE AND INJECTION DEVICE

(75) Inventors: Gareth Roberts, Wreham (GB); Sioned Owen, Denbigh (GB); Matthew Ekman, Macclesfiled (GB)

(73) Assignee: Sanofi-Aventis Deutschland GMBH, Frankfurt am Main (DE)

( * ) Notice: Subject to any disclaimer, the term of this patent is extended or adjusted under 35 U.S.C. 154(b) by 144 days.

(21) Appl. No.: 13/808,064

(22) PCT Filed: Jun. 21, 2011

(86) PCT No.: PCT/EP2011/060317
§ 371 (c)(1),
(2), (4) Date: May 14, 2013

(87) PCT Pub. No.: WO2012/000833
PCT Pub. Date: Jan. 5, 2012

(65) Prior Publication Data
US 2013/0226085 A1    Aug. 29, 2013

(30) Foreign Application Priority Data
Jul. 2, 2010   (EP) ..................................... 10168315

(51) Int. Cl.
*A61M 5/32*   (2006.01)

(52) U.S. Cl.
CPC .............. *A61M 5/322* (2013.01); *A61M 5/326* (2013.01); *A61M 5/3272* (2013.01); *A61M 5/3213* (2013.01); *A61M 2005/3267* (2013.01); *A61M 2205/59* (2013.01)

(58) Field of Classification Search
CPC .......................... A61M 5/3271; A61M 5/3272
USPC ............. 128/919; 604/164.08, 192, 195, 197, 604/198, 263
See application file for complete search history.

(56) References Cited

U.S. PATENT DOCUMENTS

| | | | |
|---|---|---|---|
| 5,279,579 A | * | 1/1994 | D'Amico .................... 604/192 |
| 5,591,138 A | * | 1/1997 | Vaillancourt ................ 604/263 |

(Continued)

FOREIGN PATENT DOCUMENTS

| | | |
|---|---|---|
| WO | 2006111864 A1 | 10/2006 |
| WO | 2006131832 A1 | 12/2006 |
| WO | 2008025179 A1 | 3/2008 |

OTHER PUBLICATIONS

Form PCT/IPEA/416, Notification of Transmittal of the International Preliminary Report on Patentability.

*Primary Examiner* — Nicholas Lucchesi
*Assistant Examiner* — Gerald Landry, II
(74) *Attorney, Agent, or Firm* — Fish & Richardson P.C.

(57) ABSTRACT

According to the invention, a safety device for a pre-filled syringe comprises a hollow support body having a releasable mounting means adapted to mount a pre-filled syringe within the support body, a hollow outer body sildably arranged with respect to the support body and adapted to receive the support body and a release collar non-rotatably arranged within the support body. The release collar is movable relative to the support body and adapted to release the mounting means. A guide track is formed into at least one substantially planar side wall of the support body. The release collar comprises at least one flexible arm with a guide pin that extends from the flexible arm and protrudes through the guide track. The guide pin is movable within and along the guide track in a plane defined by the substantially planar side wall. A guide rail is formed into at least one substantially planar inner surface of the outer body. The guide rail is adapted to abut against the guide pin to guide the movement of the guide pin along the guide track when the outer body is slid relative to the support body.

15 Claims, 8 Drawing Sheets

(56) References Cited

U.S. PATENT DOCUMENTS

| | | | |
|---|---|---|---|
| 6,379,336 B1* | 4/2002 | Asbaghi et al. | 604/192 |
| 6,692,463 B1* | 2/2004 | Marteau et al. | 604/110 |
| 6,884,237 B2* | 4/2005 | Asbaghi | 604/198 |
| 8,814,833 B2* | 8/2014 | Farrell et al. | 604/164.04 |
| 2003/0144630 A1* | 7/2003 | Chang et al. | 604/198 |
| 2004/0111064 A1* | 6/2004 | Asbaghi | 604/198 |
| 2005/0113750 A1* | 5/2005 | Targell | 604/110 |
| 2006/0135910 A1* | 6/2006 | Luther et al. | 604/110 |
| 2008/0077093 A1* | 3/2008 | Gratwohl et al. | 604/198 |
| 2009/0259178 A1* | 10/2009 | Brechbuehler et al. | 604/110 |
| 2011/0288482 A1* | 11/2011 | Farrell et al. | 604/164.04 |
| 2011/0319832 A1* | 12/2011 | Chun | 604/198 |

\* cited by examiner

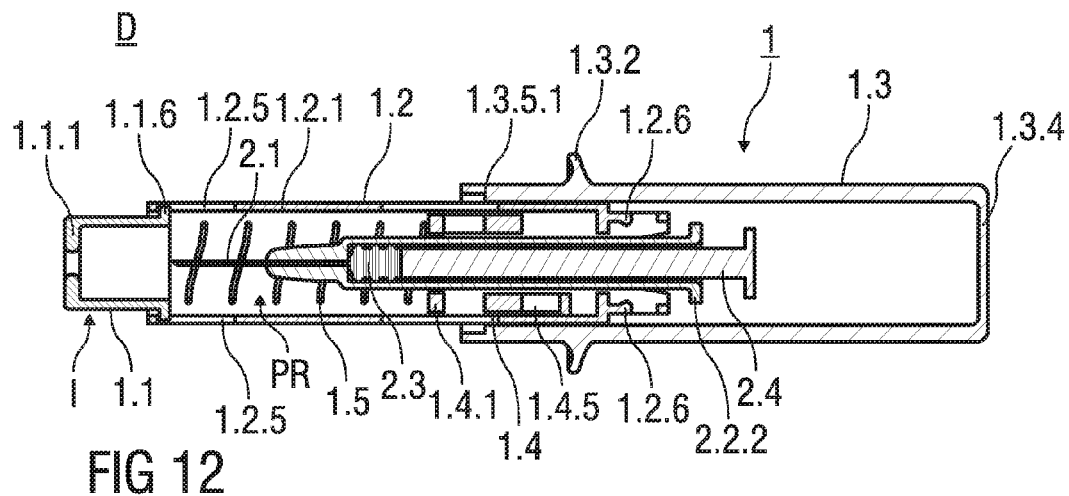
FIG 12
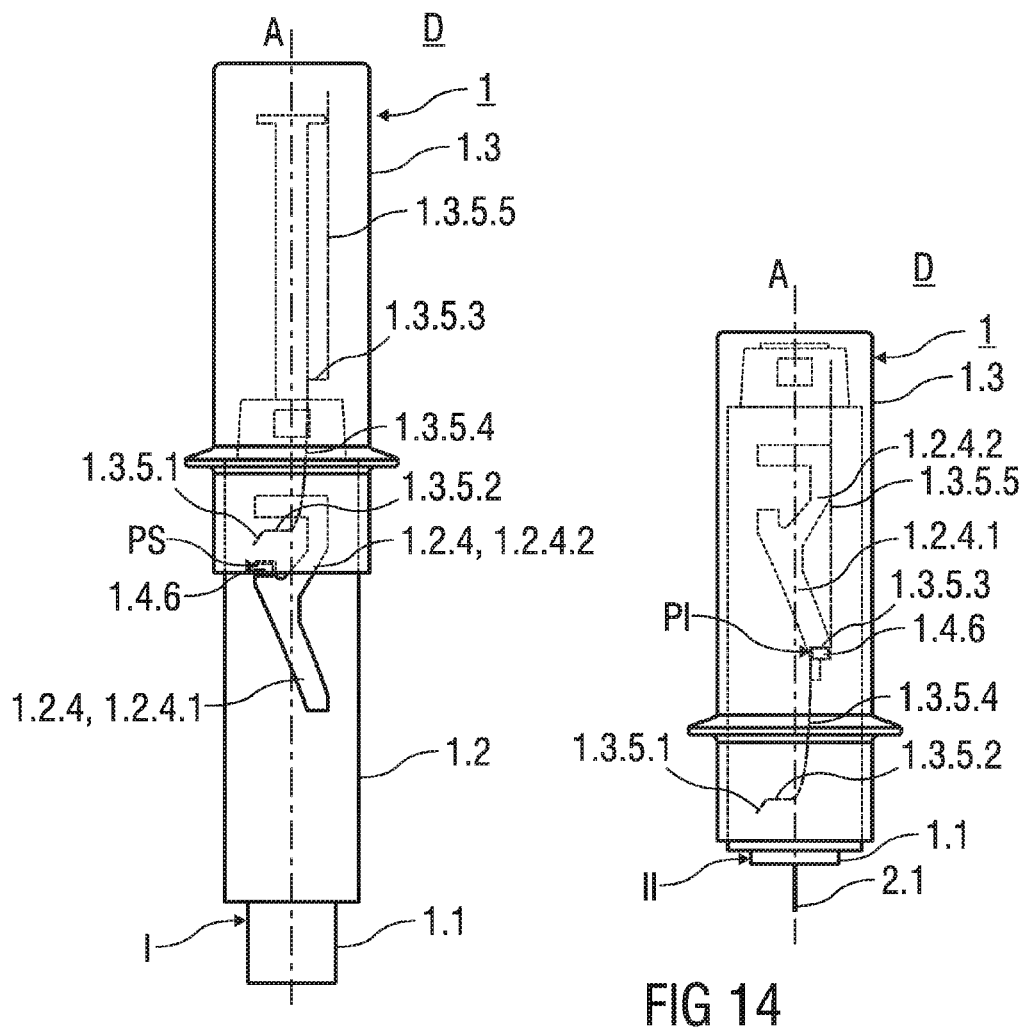
FIG 13
FIG 14

SAFETY DEVICE FOR A PRE-FILLED SYRINGE AND INJECTION DEVICE

CROSS REFERENCE TO RELATED APPLICATIONS

The present application is a U.S. National Phase Application pursuant to 35 U.S.C. §371 of International Application No. PCT/EP2011/060317 filed Jun. 21, 2011, which claims priority to European Patent Application No. 10168315.9 filed Jul. 2, 2010. The entire disclosure contents of these applications are herewith incorporated by reference into the present application.

FIELD OF INVENTION

The present invention relates to safety devices that provide needle safety and more particularly to safety devices for pre-filled syringes. The safety device is adapted to avoid accidental needle stick injuries and needle injuries before, during and after an injection of a medication or drug contained in the pre-filled syringe. In particular, the safety device provides needle safety for a subcutaneous self-administrated injection or for an injection administered by a health-care professional. The present invention further relates to injection devices comprising a pre-filled syringe.

BACKGROUND

Pre-filled syringes that are filled with a selected dosage of a medication are well known injection devices for administering the medication to a patient. Safety devices for covering a needle of a pre-filled syringe before and after use are also well known. Typically, these devices comprise a needle shield that is either manually moved or moved by the action of a relaxing spring to surround the needle.

A different type of safety devices known in the state of the art solves the object of providing needle safety by arranging the pre-filled syringe movable relative to a body, whereas the pre-filled syringe is retracted into the body after the injection.

Document WO 2006/111864 A1 describes an injection assisting device suitable for housing a syringe. The injection assistance device comprises a hollow sleeve and a sleeve tube that are able to move with respect to each other. The sleeve tube is coupled to a piston plunger. The piston plunger may be depressed into the syringe and the medicament disposed therein may be expelled by manually translating the sleeve tube with respect to the hollow sleeve. The sleeve tube further comprises a substantially planar side wall with a cam formed thereinto. A peg is coupled to the hollow sleeve by a flexible tab. The peg moves within and along the cam when the hollow sleeve and the sleeve tube are axially translated relative to each other to control the movement of the hollow sleeve. After the injection is completed, the interaction of the peg and the cam prevents any further axial displacement of the sleeve tube and the hollow sleeve so as to lock the hollow sleeve into a position wherein a needle of the syringe is covered.

The U.S. Pat. No. 5,279,579 discloses a sleeve cover that is slidably engaged to a hub of an injection needle assembly or syringe. The sleeve cover has a longitudinal groove disposed in the side wall that is adapted to guide a pin protruding radially from the hub between protective and unprotective positions.

Document US 2005/0113750 A1 a safety needle for use with a syringe. The safety needle has a cylindrical casing in which a sleeve is slidably mounted. A locking mechanism prevents re-exposure of the needle. The locking mechanism includes a plurality of fingers connected to the sleeve. At least one of the fingers has a projection that travels along a track system disposed in the inner surface of the casing when the sleeve is translated with respect to the casing.

SUMMARY

It is an object of the present invention to provide an improved safety device for a pre-filled syringe.

It is a further object of the invention to provide an improved injection device comprising a pre-filled syringe that is safe to handle and in particular prevents accidental needle stick injuries.

The object is achieved by a safety device according to claim 1 and by an injection device according to claim 15.

Preferred embodiments of the invention are given in the dependent claims.

In the context of this specification, the terms distal and proximal are defined from the point of view of a person performing an injection. Consequently, a distal direction refers to a direction pointing towards the body of a patient receiving an injection and a distal end defines an end of an element that is directed towards the body of the patient. Respectively, the proximal end of an element or the proximal direction is directed away from the body of a patient receiving the injection and opposite to the distal end or distal direction.

According to the invention, a safety device for a pre-filled syringe comprises a hollow support body having a releasable mounting means adapted to mount a pre-filled syringe within the support body, a hollow outer body sildably arranged with respect to the support body and adapted to receive the support body and a release collar non-rotatably arranged within the support body. The release collar is movable relative to the support body and adapted to release the mounting means. A guide track is formed into at least one substantially planar side wall of the support body. The release collar comprises at least one flexible arm with a guide pin that extends from the flexible arm and protrudes through the guide track. The guide pin is movable within and along the guide track in a plane defined by the substantially planar side wall. A guide rail is formed into at least one substantially planar inner surface of the outer body. The guide rail is adapted to abut against the guide pin to guide the movement of the guide pin along the guide track when the outer body is slid relative to the support body.

The support body comprises at least one substantially planar side wall, preferably two side walls opposing each other to provide a design that differs in its appearance from a standard syringe or a safety device known in the state of art. The aim is to reduce a possible patient's fear of an injection by giving the injection device comprising the safety device and the pre-filled syringe retained therein an appearance that is not connected to an injection by the typical user.

Furthermore, the safety device has only a low number of parts, so that the safety device can be cost-efficiently mass produced. The safety device is very well suited to be used in combination with disposable pre-filled syringes and disposed with the pre-filled syringe after a single injection.

The release collar moves within the support body to release the mounting means at the end of an injection stroke wherein the mounting means retain the pre-filled syringe within the support body. The movement of the release collar and the activation of the release and retraction mechanism are controlled by the guide pin moving along and interacting with the guide track formed into the substantially planar side wall of the support body. The safety device provides a simple and reliable safety mechanism that is safe and easy to handle even for inexperienced users. Apart from performing the injection stroke, no additional interaction is required from the user to activate the release and retraction mechanism. The safety device is thus very well suited for a self-administered injection of a medicament contained in the pre-filled syringe. Consequently, the patient and the user performing the injection may be one and the same person.

The guide pin extending from the flexible arm of the release collar protrudes through the guide track and is retained within the guide track in a start position prior to use of the safety device and in an end position after the injection has been carried out. The flexible arm is in an equilibrium position when the guide pin is in the start and in the end position. As the guide pin moves along the guide track during the injection, the flexible arm is laterally deflected, whereas the deflected flexible arm is stressed to bias the guide pin in a lateral direction perpendicular to a central axis of the safety device. The flexible arm releasably retains the guide pin in the start position and biases the guide pin towards the end position at the end of the injection stroke. The pre-filled syringe is kept retracted within the support body by the guide pin interacting with the guide track in the end position.

The flexible arm is connected to or integrally formed to a distal and/or a proximal end of the release collar, so that the guide pin of the flexible arm jointly moves with the release collar parallel to the central axis. Furthermore, the guide pin is allowed to be moved in the plane defined by the substantially planar side wall of the support body. According to a possible embodiment, the flexible arm in its equilibrium position extends essentially parallel to the central axis or is oriented relative to the central axis at an acute angle. The flexible arm is oriented and disposed in a manner as to bias the guide pin towards one lateral side of the safety device when the flexible arm is deflected.

In a possible embodiment of the invention, the guide pin is formed to an end of the flexible arm opposite to the end of the release collar where the flexible arm is connected to. Thus, the release collar according to the invention may comprise the flexible arm that is connected to the distal end of the release collar, whereas the flexible arm comprises the guide pin at a proximal end of the flexible arm. Alternatively, a release collar may comprise a flexible arm that is connected to the proximal end of the release collar, whereas the flexible arm comprises a guide pin at a distal end of the flexible arm. Both alternative embodiments allow for a movement of the guide pin in the plane defined by the substantially planar side wall of the support body. This minimizes the friction between the guide pin and the guide track formed into the side wall of the support body, which in turn prevents the release collar connected to the guide pin from getting stuck and jammed within the support body when the guide pin moves along the guide track.

According to another possible embodiment, the flexible arm has an arc-shaped and undulated profile. The flexible arm is laterally deflectable in a way that allows the guide pin to be moved in the plane defined by the side wall of the support body comprising the guide track, so that the friction between the guide track and the guide pin is minimized.

According to yet another embodiment of the invention, the flexible arm is connected to the release collar via a hinge, so that the flexible arm pivots about an angular segment. The release collar comprises a bearing surface that limits the pivoting movement of the flexible arm in the lateral direction, so that unintentional friction between the flexible arm and a side of the support body is prevented and the safety device can be reliably used.

In an embodiment of the invention, the guide pin is located approximately halfway between a distal end of the flexible arm and the proximal end of the flexible arm, so that the guide pin moves in the plane defined by the substantially planar side wall of the support body, whereby friction between guide pin and guide track is minimized.

The guide track formed into the side wall of the support body comprises a substantially straight first path that is oriented relative to the central axis at an acute angle and a double angled second path. The guide pin moves from the start position that is located at a proximal end of the first path in a distal direction to an intermediate position located at a distal end of the first path. The release collar jointly moves with the guide pin in the distal direction and is retained in a distal position when the guide pin is in the intermediate position.

The guide pin travels from the intermediate position in a proximal direction and is redirected into the second path. The guide pin further moves in the proximal direction along the second path until it reaches a lockout position. The release collar releases the mounting means affixing the pre-filled syringe within the support body and retracts the pre-filled syringe in a proximal direction when the guide pin moves along the second path. The release collar is retained in a proximal position when the guide pin reaches the lockout position, so that the pre-filled syringe is refracted and a hypodermic needle of the pre-filled syringe is surrounded by the support body of the safety device.

The guide pin further moves from the lockout position in a lateral direction to an end position, whereby the release collar is locked to the proximal position by the guide pin interacting with the guide track in the end position, so that a re-exposure of the hypodermic needle is prevented. The particular shape of the guide track and the interplay of the guide track with the guide pin provide a reliable release and retraction mechanism for the pre-filled syringe retained within the safety device, so that accidental needle stick injuries are avoided.

The safety device comprises a hollow outer body that receives the support body. The outer body slides relative to the support body to inject the medication contained in the pre-filled syringe through the hypodermic needle and to release and retract the pre-filled syringe retained within the safety device. The guide rail is formed into at least one substantially planar inner surface of an outer body facing the side wall of the support body with the guide track. The guide rail abuts the guide pin to guide the movement of the guide pin within the guide track when the outer body is slid relative to the support body. In particular, the guide pin is prevented from returning to its start position by the guide rail, so that a re-usage of the safety device is prevented.

The guide rail comprises a step profile with a plurality of sections that extend substantially parallel to the lateral direction and/or extend substantially parallel to the central axis and/or are oriented with respect to the central axis at an acute angle. The outer body is manually moved in distal direction to perform an injection stroke, wherein the guide rail abuts the guide pin. The step profile of the guide rail guides the guide pin within the guide track to activate the release and refraction mechanism of the safety device. Apart from performing a single linear injection stroke of the outer body towards the skin of a patient, a separate interaction to activate the release and retraction mechanism is not required.

Preferably, the support body and the outer body comprise a square or a rectangular cross-section. This is a simple way of preventing a rotation of the support body relative to the outer body, so that the injection can be conveniently executed. Furthermore, the angular shaped design significantly differs from traditional designs of syringes and/or safety devices for pre-filled syringes, which makes it mentally easier to perform a self-administered injection for patients that fear injections.

The guide pin moves within the guide track from the start position to the intermediate position and further to the lockout position. The flexible arm is deflected and stressed when the guide pin is in the lockout position. As the flexible arm is typically made from a resilient plastics material that is prone to material fatigue, it is advantageous to deflect and stress the flexible arm during use of the safety device. This allows for an extended shelf life of the safety device. The guide pin is moved from the lockout position to the end position by the action of the relaxing deflected flexible arm, so that the flexible arm is in an equilibrium position when the guide pin is in the end position locking the release collar to the proximal position, so that the hypodermic needle is prevented from re-exposure even after prolonged periods.

A needle shield is retained within and slidable relative to the support body that comprises a second spring seat located at a proximal end of the needle shield. A compression spring is arranged within the support body that bears against the second spring seat of the needle shield in the distal direction and against a first spring seat of the release collar in the proximal direction. The needle shield is biased in a distal direction towards a first position, in which the hypodermic needle is surrounded by the needle shield. The needle shield is pressed against the skin of the patient, whereby the needle shield is moved towards a refracted position and the needle shield punctures the skin of a patient.

According to a possible embodiment, the needle shield is made from an opaque plastics material. The hypodermic needle is hidden from the patient's view before the injection by the needle shield that is retained in the initial position. This eases a possible patient's fear of needles. The safety device is thus particularly suited for performing self-administered injections.

According to an alternative embodiment, the needle shield is made from a transparent plastics material. A healthcare professional that uses the safety device thus can visually confirm the correct placement of the hypodermic needle penetrating the skin of the patient even when the hypodermic needle is surrounded by the needle shield.

As the safety device is both suited for self-administered injections and injections carried out by a healthcare professional, the person referred to as the user or the patient may be one and the same person.

According to a possible embodiment of the invention, the needle shield comprises a square or a rectangular cross-section to prevent a relative rotation between needle shield and support body during the injection. As the needle shield rests onto the skin of a patient, this avoids unnecessary pain caused to a patient in particular when the needle still penetrates the skin.

The needle shield further comprises an opening part of resilient plastics material that is concentrically arranged around a central opening of the needle shield. The hypodermic needle protrudes through the central opening during the injection. The hypodermic needle is covered by a needle cap prior to use of the safety device, wherein the needle cap protrudes through the central opening and deflects the opening part outwardly. After the removal of the needle cap, the opening part unbends and expands inwardly, so that a diameter of the central opening is reduced. This in turn avoids accidental needle stick injuries, as the opening of reduced diameter prevents an inadvertent contact with the hypodermic needle.

The release collar moves in a proximal direction by the action of the relaxing compression spring, whereby the release collar automatically releases the mounting means of the support body. The pre-filled syringe is automatically released and retracted by the proximal movement of the release collar after the injection has been performed.

An injection device comprises a pre-filled syringe retained in the support body of the safety device. The pre-filled syringe comprises a hypodermic needle attached to a distal end of the pre-filled syringe, a barrel with an inner cavity in fluid communication with the hypodermic needle and a piston fluid-tightly sealing a proximal end of the inner cavity. The piston is movable by actuating a piston rod protruding a proximal end of the barrel. The pre-filled syringe is releasably mounted by the mounting means within the support body of the safety device, so that the pre-filled syringe can be retracted to cover the hypodermic needle after the injection. The injection device comprising the pre-filled syringe and the safety device combines the aforementioned advantages and avoids inadvertent needle sticks before, during and after an injection delivering the medication beneath the skin of patient.

Further scope of applicability of the present invention will become apparent from the detailed description given hereinafter. However, it should be understood that the detailed description and specific examples, while indicating possible embodiments of the invention, are given by way of illustration only, since various changes and modifications within the spirit and scope of the invention will become apparent to those skilled in the art from this detailed description.

BRIEF DESCRIPTION OF THE DRAWINGS

The present invention will be better understood from the detailed description given in the following. The accompanying drawings are given for illustrative purposes only and do not limit the scope of the present invention.

FIG. 12 shows a second sectional view of an injection device with a pre-filled syringe in a retracted position.

FIG. 13 schematically shows a side view of the safety device before usage indicating a location of a guide pin within a guide track and relative to a guide rail.

FIG. 14 schematically shows a side view of an injection device at the end of an injection stroke indicating an intermediate position of a guide pin within a guide track and relative to a guide rail.

Corresponding parts are marked with the same reference symbols in all figures.

DETAILED DESCRIPTION

Figure 1:
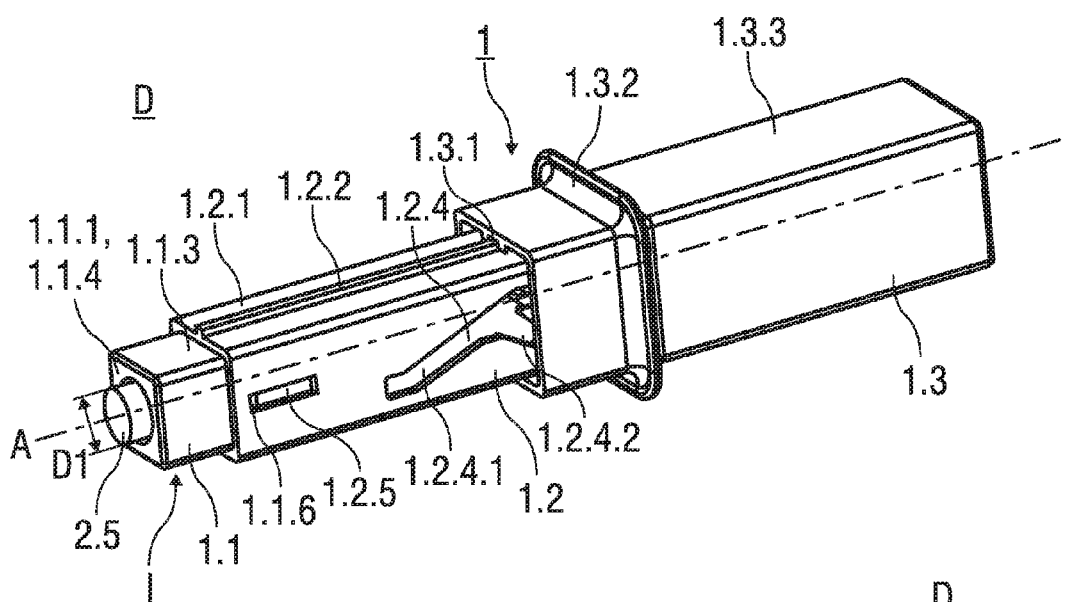
FIG. 1 shows a perspective view of an injection device comprising a safety device and a pre-filled syringe before usage.

FIG. 1 shows an injection device D in a packaged state as it would be presented to a user performing an injection. The injection device D comprises a safety device 1 and a pre-filled syringe 2. The safety device 1 comprises a hollow needle shield 1.1 with a substantially square cross-section.

Alternatively, the needle shield 1.1 may have a substantially rectangular cross-section or be of conventional cylindrical form with a circular cross-section.

Additionally, the needle shield 1.1 may comprise an outwardly protruding flange that rests on the skin of a patient during the injection.

The needle shield 1.1 is received within a hollow support body 1.2 with a substantially square cross-section, whereas the needle shield 1.1 is slidable with respect to the support body 1.2 between a first position I and a second position II parallel to the central axis A of the safety device 1. Prior to use of the safety device 1, the needle shield 1.1 is retained in the first position I, wherein the needle shield 1.1 protrudes the support body 1.2.

The injection device D comprises the safety device 1 with a pre-filled syringe 2 retained therein. The pre-filled syringe 2 is releasably retained within the support body 1.2 in an advanced position PA, so that a hypodermic needle 2.1 of the pre-filled syringe 2 protrudes the support body 1.2 in a distal direction. The needle shield 1.1 in the first position I surrounds and hides the hypodermic needle 2.1 from the view of the user when the pre-filled syringe 2 is retained in the advanced position PA.

FIG. 1 shows a hollow outer body 1.3 with a closed proximal and an open distal end sized to receive the support body 1.2. The proximal end of the support body 1.2 is received within the open distal end of the outer body 1.3, whereas the outer body 1.3 is slidable relative to the support body 1.2 parallel to the central axis A.

The outer body 1.3 comprises a cross-section that corresponds to the cross-section of the support body 1.2 to prevent a relative rotation of these parts 1.2, 1.3 when the outer body 1.3 is slid relative to the support body 1.2. In the embodiment shown in FIG. 1, the outer body 1.3 has a substantially square cross-section. In an alternative embodiment, the outer body 1.3 comprises a substantially rectangular cross-section.

The support body 1.2 comprises four substantially planar side walls 1.2.1. Respectively, the outer body 1.3 comprises four substantially planar inner surfaces facing the planar side walls 1.2.1 of the support body 1.2.

Figure 8:
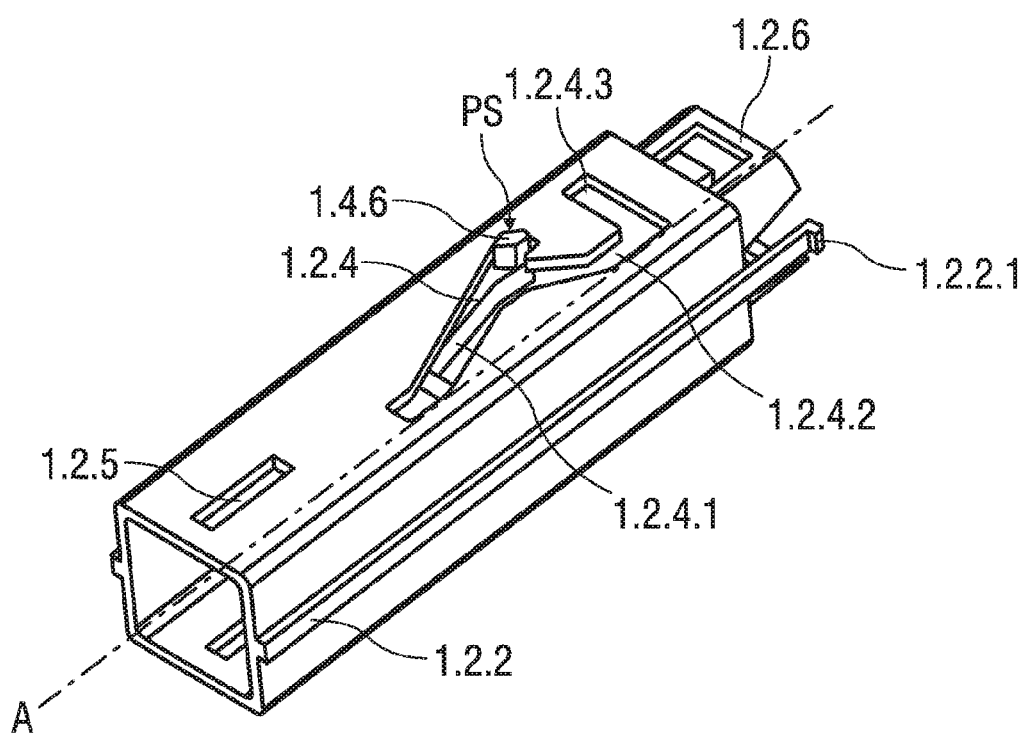
FIG. 8 shows a perspective view of a support body with a release collar received therein.

As shown in FIG. 1 and in more detail in FIG. 8, a guide track 1.2.4 in the form of a slot of complicated shape is formed into the side wall 1.2.1 of the support body 1.2. The guide track 1.2.4 comprises a substantially straight first path 1.2.4.1 that is oriented at an acute angle relative to the central axis A and a double angled second path 1.2.4.2. The double angled second path 1.2.4.2 comprises three sections, wherein adjacent sections are oriented at an angle with respect each other.

At least one inner surface of the outer body 1.3 facing one of the side walls 1.2.1 of the support body 1.2 comprises means to prevent jamming of the outer body 1.3 and the support body 1.2 when slid relative to each other. At least one longitudinal tongue 1.2.2 axially extending along a substantial length of the support body 1.2 and parallel to the central axis A is integrally formed to an exterior surface of the at least one side wall 1.2.1 of the support body 1.2. The longitudinal tongue 1.2.2 is received in a corresponding longitudinal groove 1.3.1 formed into the at least one interior surface of the outer body 1.3.

Figure 3:
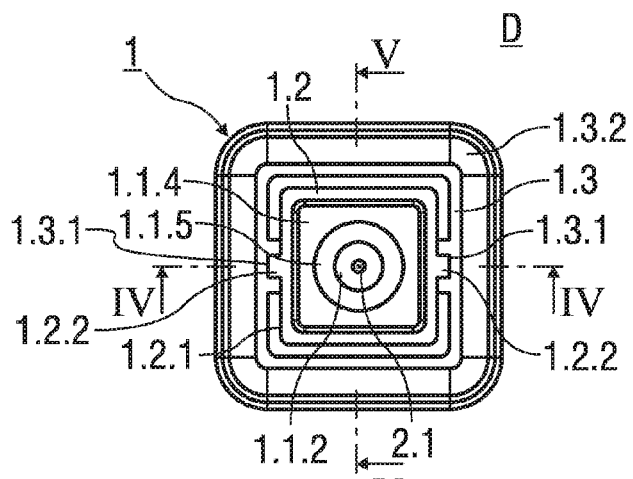
FIG. 3 shows a plan view of an injection device from a distal end of the safety device.

According to a possible embodiment, the support body 1.2 comprises two longitudinal tongues 1.2.2, as best seen in FIG. 3, formed to two opposing side walls 1.2.1. Respectively, the outer body 1.3 comprises two longitudinal grooves 1.3.1 formed into two opposing inner surfaces of the outer body 1.3.

Figure 2:
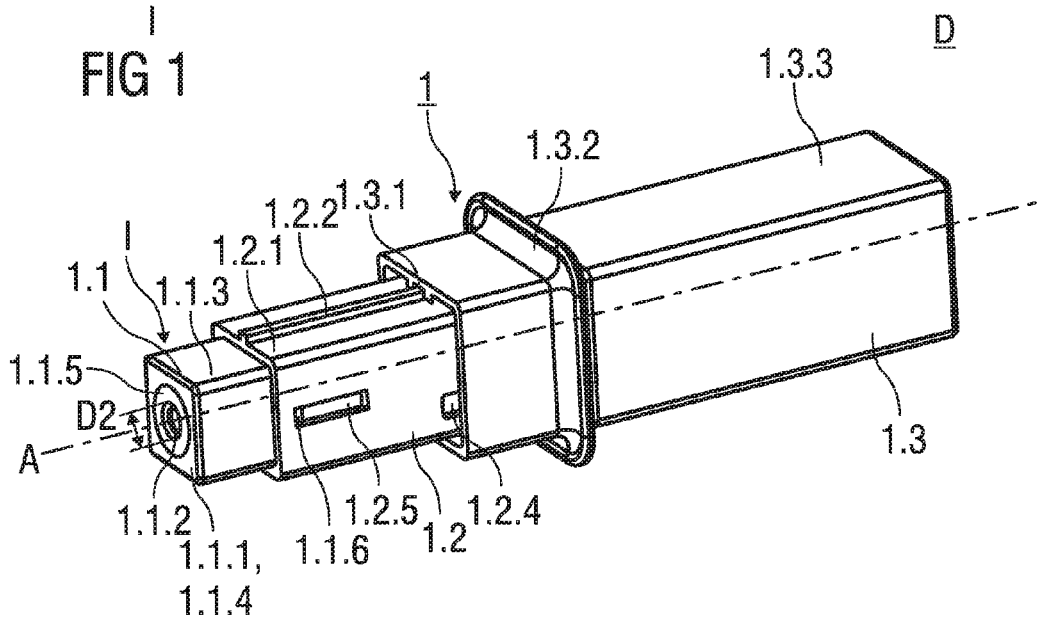
FIG. 2 shows a perspective view of an injection device comprising a safety device and a pre-filled syringe after removal of a needle cap.

FIGS. 1 and 2 show a circumferential hand flange 1.3.2 that is integrally formed to the outer body 1.3 close to its distal end to allow a proximal section 1.3.3 of the outer body 1.3 to be gripped by a hand of the user performing an injection stroke.

A distal surface 1.1.1 of the needle shield 1.1 is orientated perpendicular to the central axis A and forms the distal end of the needle shield 1.1. The distal surface 1.1.1 is designed to rest onto the skin of a patient during the injection and comprises a circular central opening 1.1.2, whereas a centre of the central opening 1.1.2 is aligned on the central axis A. As can be seen in FIG. 1, the central opening 1.1.2 has a first inner diameter D1 corresponding to an outer diameter of a needle cap 2.5 frictionally held on a distal end of the pre-filled syringe 2, whereas the needle cap 2.5 covers the hypodermic needle 2.1 prior to the injection. The needle cap 2.5 distally protrudes beyond the distal surface 1.1.1, so that the needle cap 2.5 can be manually removed before usage of the safety device 1.

The safety device 1 comprises penetration depth limiting means to limit the penetration depth of the hypodermic needle 2.1 in particular during an intramuscular or subcutaneous injection. The penetration depth limiting means comprise two limiter catches 1.1.6 connected to the needle shield 1.1, whereas each limiter catch 1.1.6 moves within a limiter recess 1.2.5 formed into opposing side walls 1.2.1 and extending parallel to the central axis A for an axial distance that corresponds to the penetration depth.

The needle shield 1.1 is made from two materials of different flexibility. Shield side walls 1.1.3 and a peripheral part 1.1.4 of the distal surface 1.1.1 are made from a relatively stiff plastics material.

As best seen in FIG. 2, the distal surface 1.1.1 comprises an opening part 1.1.5 adjacent to the central opening 1.1.2. The opening part 1.1.5 is made from a resilient and stretchable plastics material like silicone or silicone elastomer. The central opening 1.1.2 has variable width. When the needle cap 2.5 is attached to the pre-filled syringe 2 and received inside the central opening 1.1.2, the opening part 1.1.5 stretches around the needle cap 2.5 to frictionally hold the needle cap 2.5 in the central opening 1.1.2. After removal of the needle cap 2.5, the flexible material of the opening part 1.1.5 unbends and expands as a consequence of the stress relief resulting in a central opening 1.1.2 with reduced width and smaller second inner diameter D2. The second inner diameter D2 of the central opening 1.1.2 is dimensioned to allow the hypodermic needle 2.1 to protrude through the central opening 1.1.2, whereas a finger of a person is prevented to enter the interior through the central opening 1.1.2 to avoid needle stick injuries.

Figure 4:
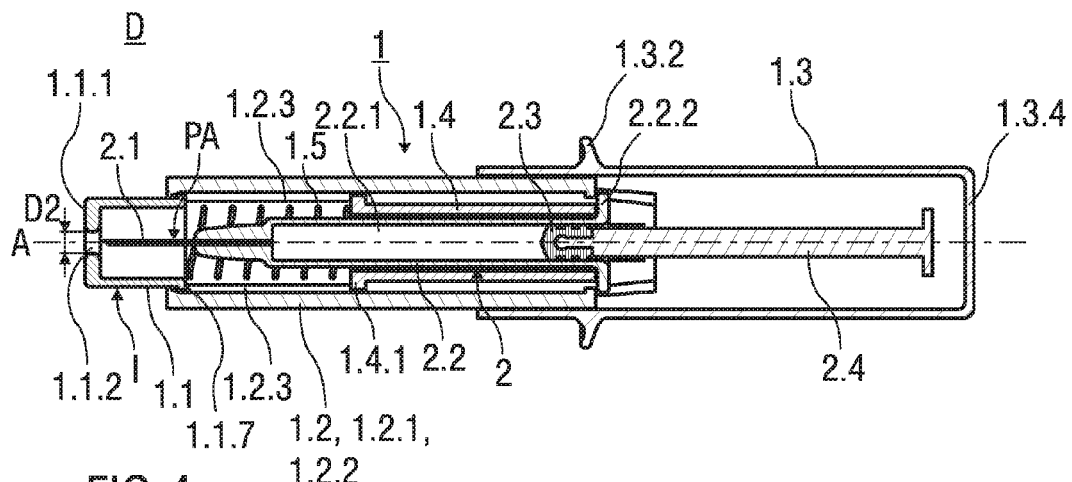
FIG. 4 shows a sectional view of an injection device after removal of the needle cap according to a first cross-section.
Figure 5:
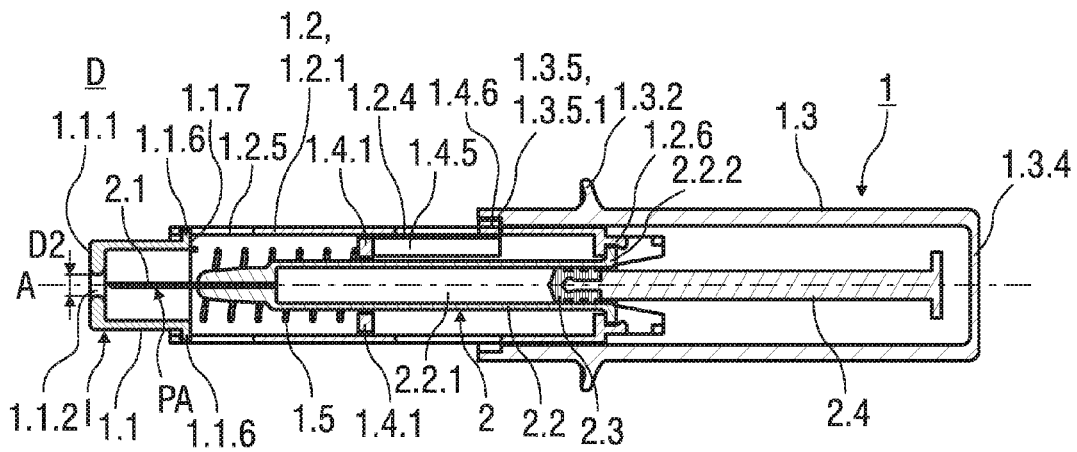
FIG. 5 shows a sectional view of an injection device after removal of the needle cap according to a second cross-section.

FIGS. 4 and 5 show sectional views of the injection device D according to a first cross-section IV and a second cross-section V indicated in FIG. 3. The pre-filled syringe 2 is retained within the safety device 1 in the advanced position PA, so that the hypodermic needle 2.1 protrudes the support body 1.2. The pre-filled syringe 2 is received in a release collar 1.4 which is slidable relative to the support body 1.2 and parallel to the central axis A.

As best seen in FIG. 4, the pre-filled syringe 2 retained within the safety device 1 comprises the hypodermic needle 2.1, a barrel 2.2 having an inner cavity 2.2.1 containing a medication, a piston 2.3 which provides a liquid-tight seal of a proximal end of the inner cavity 2.2.1 and a piston rod 2.4 connected to the piston 2.3. The inner cavity 2.2.1 is in fluid communication with the hypodermic needle 2.1 and the piston 2.3 is movable by actuating the piston rod 2.4.

FIG. 4 shows the injection device D at the beginning of the injection. A first spring seat 1.4.1 is formed to the release collar 1.4 at a distal end. A compression spring 1.5 is arranged between the needle shield 1.1 and the release collar 1.4 in a slightly energized state sufficient to bias the needle shield 1.1 distally to avoid unintentional exposure of the hypodermic needle 2.1. The compression spring 1.5 bears against a second spring seat 1.1.7 of the needle shield 1.1 in the distal direction and against the first spring seat 1.4.1 in the proximal direction, so that the needle shield 1.1 and the release collar 1.4 are biased away from each other. The needle shield 1.1 is retained in the first position I surrounding the hypodermic needle 2.1 of the pre-filled syringe 2.

Figure 6A:
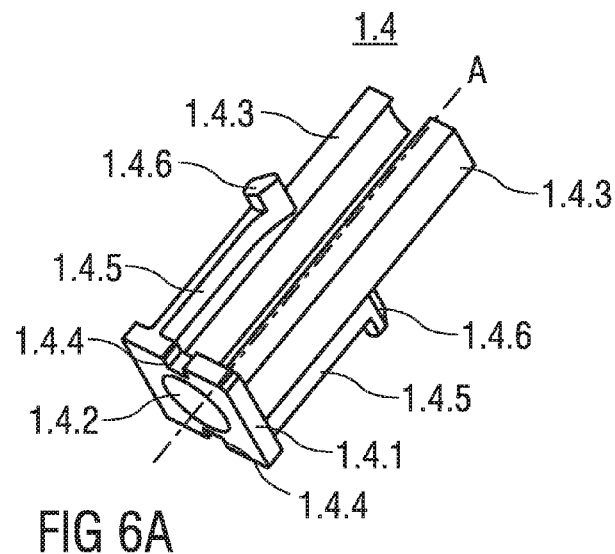
FIG. 6A shows a perspective view of a release collar according to a first embodiment adapted to receive a pre-filled syringe.

According to a possible embodiment shown in more detail in FIG. 6A, the first spring seat 1.4.1 comprises two notches 1.4.4 formed into opposing sides of the first spring seat 1.4.1. As illustrated in FIG. 4, each notch 1.4.4 receives a corresponding inner tongue 1.2.3. The inner tongue 1.2.3 is formed to an inner surface of the side wall 1.2.1 to facilitate the sliding movement of the release collar 1.4 relative to the support body 1.2.

FIG. 5 shows a sectional view of the injection device D according to the second cross-section V. The release collar 1.4 comprises a flexible arm 1.4.5. A guide pin 1.4.6 is formed to the flexible arm 1.4.5 that protrudes through the guide track 1.2.4 and beyond the side wall 1.2.1. A guide rail 1.3.5 is formed into an inner surface of the outer body 1.3 that abuts the protruding guide pin 1.4.6 to guide the movement of the guide pin 1.4.6 along the guide track 1.2.4.

Before the injection, the piston rod 2.4 is kept at a distance from a proximal end wall 1.3.4 of the outer body 1.3 to avoid unintentional activation of the piston rod 2.4.

The pre-filled syringe 2 is releasably retained within the support body 1.2 of the safety device 1. The support body 1.2 comprises resilient mounting means 1.2.6 at the proximal end of the support body 1.2 that clamp to a barrel collar 2.2.2 of the barrel 2.2 to releasably retain the pre-filled syringe 2 within the support body 1.2.

FIGS. 6A to 6D show in detail the release collar 1.4 according to different embodiments of the invention.

FIG. 6A shows the release collar according to a first embodiment with the first spring seat 1.4.1 formed to its distal end. The first spring seat 1.4.1 comprises a substantially square cross-section and a central bore 1.4.2, which is centered on the central axis A when the release collar 1.4 is assembled within the support body 1.2. The width of the circular central bore 1.4.2 corresponds to or is slightly bigger than the width of the substantially cylindrical barrel 2.2 of the pre-filled syringe 2, which may be inserted in the release collar 1.4. Two clamp arms 1.4.3 opposing each other proximally extend from the first spring seat 1.4.1 parallel to the central axis A. The barrel 2.2 may be received between the two opposing clamp arms 1.4.3 that are adapted to engage the barrel 2.2, whereas the barrel 2.2 is allowed to be slid relative to the release collar 1.4 and parallel to the central axis A.

The release collar 1.4 comprises two diagonally opposing flexible arms 1.4.5 that proximally extend from the first spring seat 1.4.1 and that are substantially parallel to the central axis A. The flexible arms 1.4.5 are made from a resilient plastics material and are deflectable in a lateral direction perpendicular to the central axis A. FIG. 6A shows the flexible arms 1.4.5 in their equilibrium positions substantially parallel to the central axis A. When the flexible arms 1.4.5 are laterally deflected, they are biased towards the equilibrium position.

The flexible arm 1.4.5 is connected to the first spring seat 1.4.1 near a corner of the first spring seat 1.4.1, so that the flexible arm 1.4.5 extends parallel to but laterally displaced from the central axis A. Each flexible arm 1.4.5 comprises one guide pin 1.4.6 at its proximal end. The guide pin 1.4.6 extends perpendicular to the side wall 1.2.1 when the release collar 1.4 is assembled within the support body 1.2. When the flexible arm 1.4.5 is laterally deflected, the guide pin 1.4.6 is moved in a plane parallel to the side wall 1.2.1 of the support body 1.2.

Figure 6B:
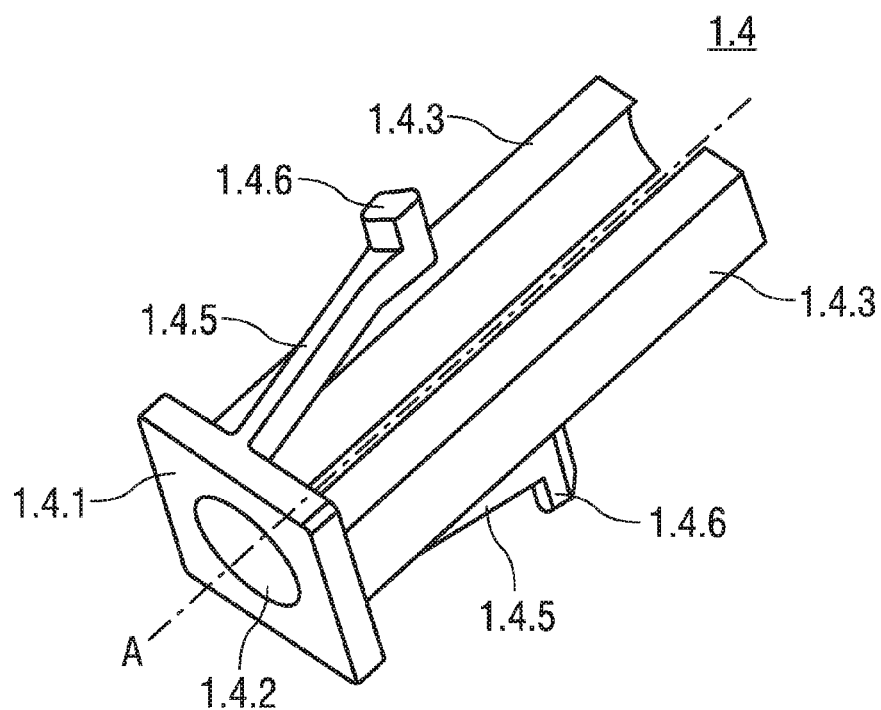
FIG. 6B shows a perspective view of a release collar according to a second embodiment adapted to receive a pre-filled syringe.

FIG. 6B shows a modification of the release collar 1.4 according to a second embodiment. The flexible arm 1.4 is oriented relative to the central axis A at an acute angle. The first spring seat 1.4.4 comprises a square cross-section.

Additionally, the first spring seat 1.4.4 may comprise the notch 1.4.4 that receives the inner tongue 1.2.3 to avoid a jamming of the release collar 1.4 within the support body 1.2 when the release collar 1.4 is slid within the support body 1.2.

Figure 6C:
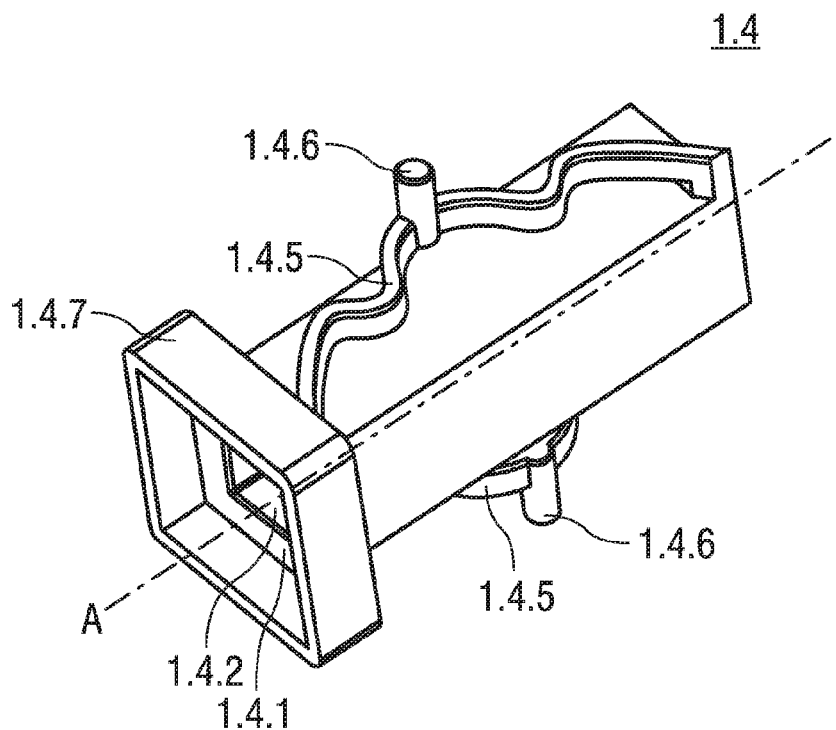
FIG. 6C shows a perspective view of a release collar according to a third embodiment adapted to receive a pre-filled syringe.

FIG. 6C shows the release collar 1.4 according to a third embodiment. The flexible arm 1.4.5 has an arc-shaped and undulated profile and is connected to the first spring seat 1.4.1 at the distal end of the release collar 1.4 and to a proximal end of the release collar 1.4. The guide pin 1.4.6 extends from the flexible arm 1.4.5 and is located approximately halfway between a distal and a proximal end of the flexible arm 1.4.5.

The release collar 1.4 has a tubular shape with a square cross-section, whereas the central bore 1.4.2 of the release collar 1.4 is sized to surround the barrel 2.2 of the pre-filled syringe 2. The release collar 1.4 comprises a circumferential shroud 1.4.7 that prevents the compression spring 1.5 from getting jammed between the support body 1.2 and the release collar 1.4 during use of the safety device 1.

Figure 6D:
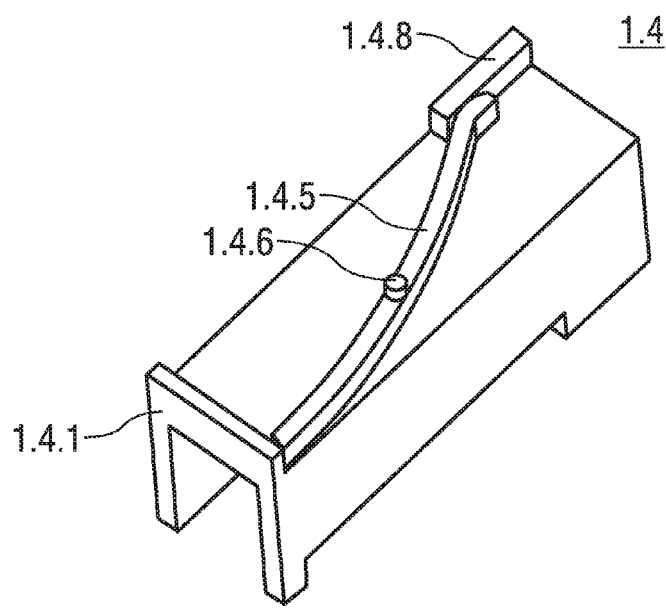
FIG. 6D shows a perspective view of a release collar according to a forth embodiment adapted to receive a pre-filled syringe.

The release collar 1.4 according to a fourth embodiment of the invention is illustrated in FIG. 6D. The release collar 1.4 has a substantial tubular shape and comprises three side walls and one open side. The guide pin 1.4.6 is centrally arranged on the flexible arm 1.4.5 between the distal and the proximal end thereof. The flexible arm 1.4.5 is connected to the first spring seat 1.4.1 via a hinge that allows the flexible arm to pivot in the lateral direction, whereas the guide pin 1.4.6 moves in a plane parallel to the side wall 1.2.1 of the support body 1.2. The release collar 1.4 comprises a bearing surface 1.4.8 that limits the pivoting movement of the flexible arm 1.4.5, so that the proximal end of the flexing arm 1.4.5 is spaced away from one of the side walls 1.2.1.

Figure 7:
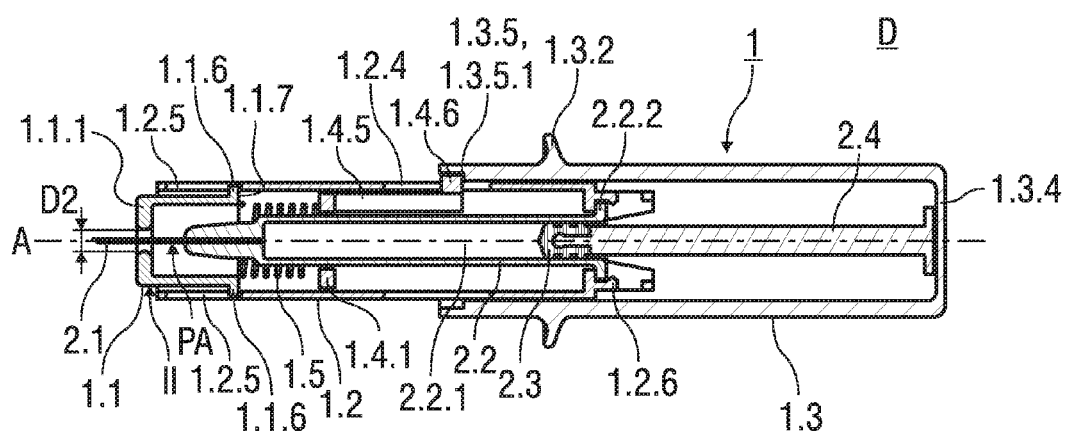
FIG. 7 shows a sectional view of an injection device at the beginning of an injection stroke delivering a medication.

FIG. 7 shows a sectional view of the injection device D at the beginning of the injection stroke. The proximal end wall 1.3.4 of the outer body 1.3 abuts the proximal end of the piston rod 2.4. The needle shield 1.1 is pushed proximally to a second position II, whereby the hypodermic needle 2.1 of the pre-filled syringe 2 is exposed and the compression spring 1.5 is partially compressed and partially energized.

The guide rail 1.3.5 formed into the inner surface of the outer body 1.3 abuts the protruding guide pin 1.4.6 to guide the movement of the guide pin 1.4.6 along the guide track 1.2.4. The guide rail 1.3.5 comprises a step profile with several sections that are differently oriented relative to the central axis A.

FIG. 8 shows a perspective view of the support body 1.2 with the release collar 1.4 received therein. The guide pin 1.4.6 is retained within the guide track 1.2.4 in the start position PS. The guide track 1.2.4 comprises the straight first path 1.2.4.1 that is oriented at an acute angle relative to the central axis A and a double angled second path 1.2.4.2. The second path 1.2.4.2 comprises an end section 1.2.4.3 that extends perpendicular to the central axis A in the lateral direction.

The longitudinal tongue 1.2.2 formed to the support body 1.2 comprises an outward projection 1.2.2.1. The longitudinal tongue 1.2.2 travels along a recess (not illustrated) formed into the inner surface of the outer body 1.3 when the outer body 1.3 is slid relative to the support body 1.2. A proximal movement of the outer body 1.3 with respect to the support body 1.2 is limited by the outward projection 1.2.2.1 abutting a distal end of the recess formed into the inner surface of the outer body 1.3.

Figure 9:
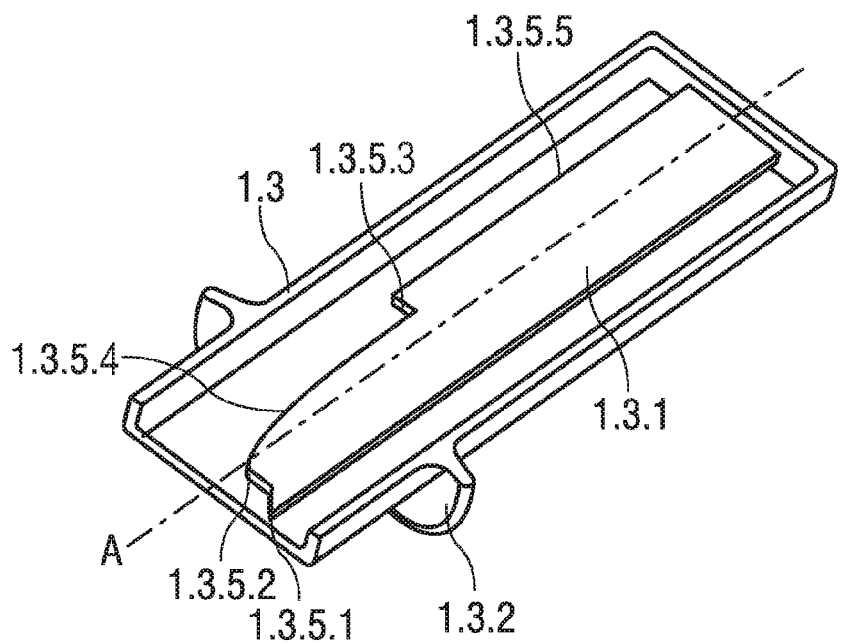
FIG. 9 shows details of a guide rail formed into an inner surface of an outer body.

FIG. 9 shows details of the guide rail 1.3.5 formed into the inner surface of the outer body 1.3 facing the inner side wall 1.2.1 comprising the guide track 1.2.4. Starting from the distal end, the guide rail 1.3.5 comprises a relative short inclined section 1.3.5.1 that is oriented at an acute angle relative to the central axis A, a first lateral section 1.3.5.2, a first axial section 1.3.5.4 that is slightly curved but extends substantially parallel to the central axis A, a second lateral section 1.3.5.3 and second axial section 1.3.5.5 parallel to the central axis A and located at a proximal end of the guide rail 1.3.5.

The injection is carried out by orientating the central axis A essentially perpendicularly to a skin surface of a patient, whereas the distal surface 1.1.1 of the needle shield 1.1 abuts the skin surface of the patient.

In the first stage of the injection, the distal surface 1.1.1 is placed onto the skin of the patient and proximally pressed against the biasing force of the compression spring 1.5 until the limiter catch 1.1.6 reaches and is stopped by a proximal end of the limiter recess 1.2.5. The hypodermic needle 2.1 penetrates the skin of the patient.

The proximal end wall 1.3.4 of the outer body 1.3 abuts the proximal end of the piston rod 2.4, so that the piston 2.3 can be pushed in a distal direction by moving the outer body 1.3 towards the skin surface.

In the second stage of the injection, the injection stroke is carried out by pushing the outer body 1.3 in the distal direction towards the skin surface of the patient. As shown in FIG. 7, the inclined section 1.3.5.1 abuts the guide pin 1.4.6 at the beginning of the injection stroke. The outer body 1.3 is distally pushed, so that the guide pin 1.4.6 leaves a start position PS, as best seen in FIG. 13, in a distal and in a lateral direction, until the guide pin 1.4.6 abuts the first lateral section 1.3.5.2. The first lateral section 1.3.5.2 guides the guide pin 1.4.6 further in the distal direction. The release collar 1.4 moves relative to the pre-filled syringe 2 and relative to the support body 1.2 in a distal direction, whereby the guide pin 1.4.6 distally moves from the start position PS, as shown in FIG. 13, within the first path 1.2.4.1 of the guide track 1.2.4.

The distal movement of the outer body 1.3 causes both the medication contained in the inner cavity 2.2.1 to be expelled through the hypodermic needle 2.1 and the release collar 1.4 to be moved relative to the pre-filled syringe 2 and relative to the support body 1.2 in a distal direction, whereby the compression spring 1.5 is compressed and thus further energized. The guide pin 1.4.6 moves within the first path 1.2.4.1 of the guide track 1.2.4 in a distal direction. During this movement of the guide pin 1.4.6, the flexible arm 1.4.5 is deflected in a lateral direction perpendicular to the central axis A until the guide pin 1.4.6 reaches an intermediate position PI located at a distal end of the first path 1.2.4.1 at the end of the injection stroke.

Figure 10:
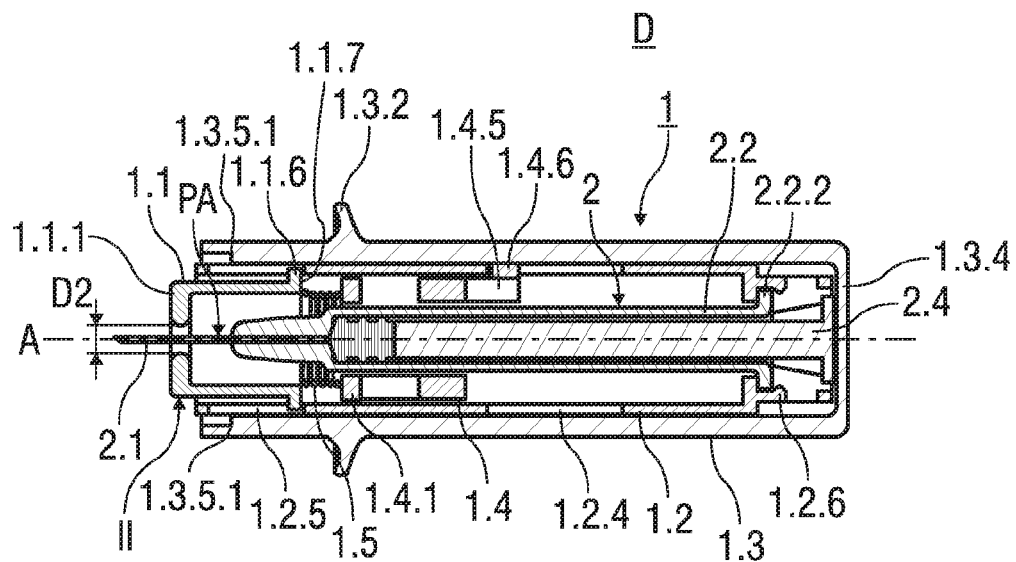
FIG. 10 shows a sectional view of an injection device at the end of an injection stroke delivering a medication.

FIG. 10 shows the injection device D at the end of the injection stroke when the guide pin 1.4.6 reached the intermediate position PI at the distal end of the first path 1.2.4.1. The guide pin 1.4.6 is laterally deflected beyond a lateral expansion of the first lateral section 1.3.5.2 and abuts the second lateral section 1.3.5.3 of the guide rail 1.3.5, as best shown in FIG. 14. The second lateral section 1.3.5.3 of the guide rail 1.3.5 retains the guide pin 1.4.6 in the intermediate position PI. The second lateral section 1.3.5.3 perpendicularly extends to the central axis A and is displaced from the first lateral section 1.3.5.3 by both an axial distance in a proximal direction and a lateral distance. The flexible arm 1.4.5 is maximally deflected in a lateral direction and thus biased toward its equilibrium position. A first axial section 1.3.5.4 of the guide rail 1.3.5 that abuts the guide pin 1.4.6 in a lateral direction prevents the flexible arm 1.4.5 from returning to its equilibrium position. The first axial section 1.3.5.4 extends substantially parallel to the central axis A between the first lateral section 1.3.5.2 and the second lateral section 1.3.5.3 of the guide rail 1.3.5.

The compression spring 1.5 is fully compressed and fully energized at the end of injection stroke biasing the needle shield 1.1 in a distal direction and the release collar 1.4 in a proximal direction. This biasing force is counteracted by a force exerted by the user performing the injection, who presses the outer body 1.3 distally towards the distal surface 1.1.1 that rests on the skin of a patient.

Upon relieving this force exerted by the user, the compression spring 1.5 relaxes, whereby the needle shield 1.1 is moved distally towards the first position I by the action of the relaxing compression spring 1.5. The release collar 1.4 is moved within the support body 1.2 by the action of the relaxing compression spring 1.5 in a proximal direction. At the same time the guide pin 1.4.6 proximally travels within a section of the first path 1.2.4.1 and further within the second path 1.2.4.2 of the guide track 1.2.4. As the guide pin 1.4.6 abuts the second lateral section 1.3.5.3 of the guide rail 1.3.5, the outer body 1.3 is pushed in a proximal direction.

While the guide pin 1.4.6 moves in a proximal direction, it abuts the first axial section 1.3.5.4 of the guide rail 1.3.5 in a lateral direction preventing the guide pin 1.4.6 to return to its start position PS and guiding the guide pin 1.4.6 to enter the second path 1.2.4.2 of the guide track 1.2.4.

Figure 11:
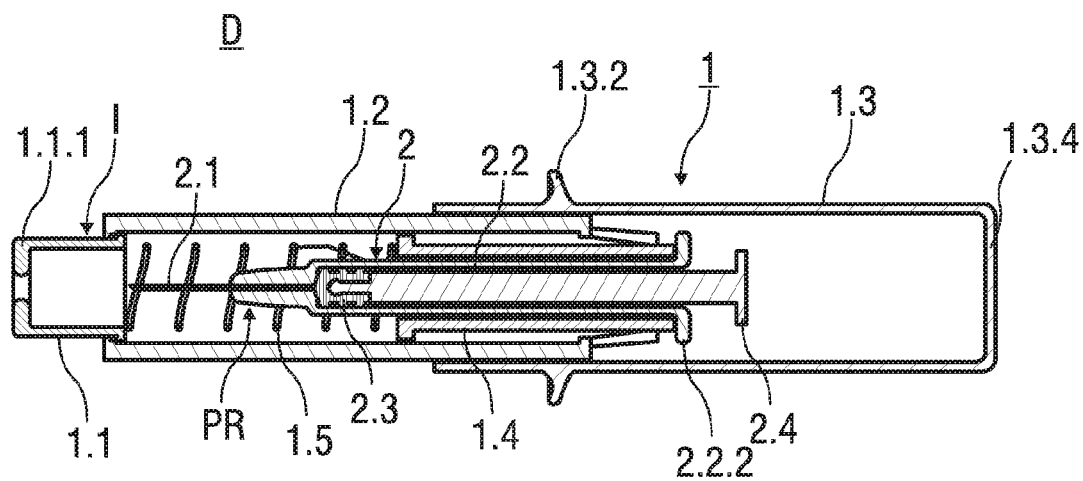
FIG. 11 shows a first sectional view of an injection device with a pre-filled syringe in a retracted position.

The release collar 1.4 moves proximal within the support body 1.2 until the release collar 1.4, as best seen in FIG. 11, abuts the barrel collar 2.2.2. As shown in FIG. 12, the mounting means 1.2.6 mounting the pre-filled syringe 2 relative to the support body 1.2 are released by a spring force exerted by the compression spring 1.5 upon the barrel collar 2.2.2 in a proximal direction. The pre-filled syringe 2 proximally moves by the action of the relaxing compression spring to a retracted position PR, wherein the distal tip of the hypodermic needle 2.1 is surrounded by the support body 1.2. In the retracted position PR, the pre-filled syringe 2 is retracted within the support body 1.2 and the outer body 1.3.

Figure 15:
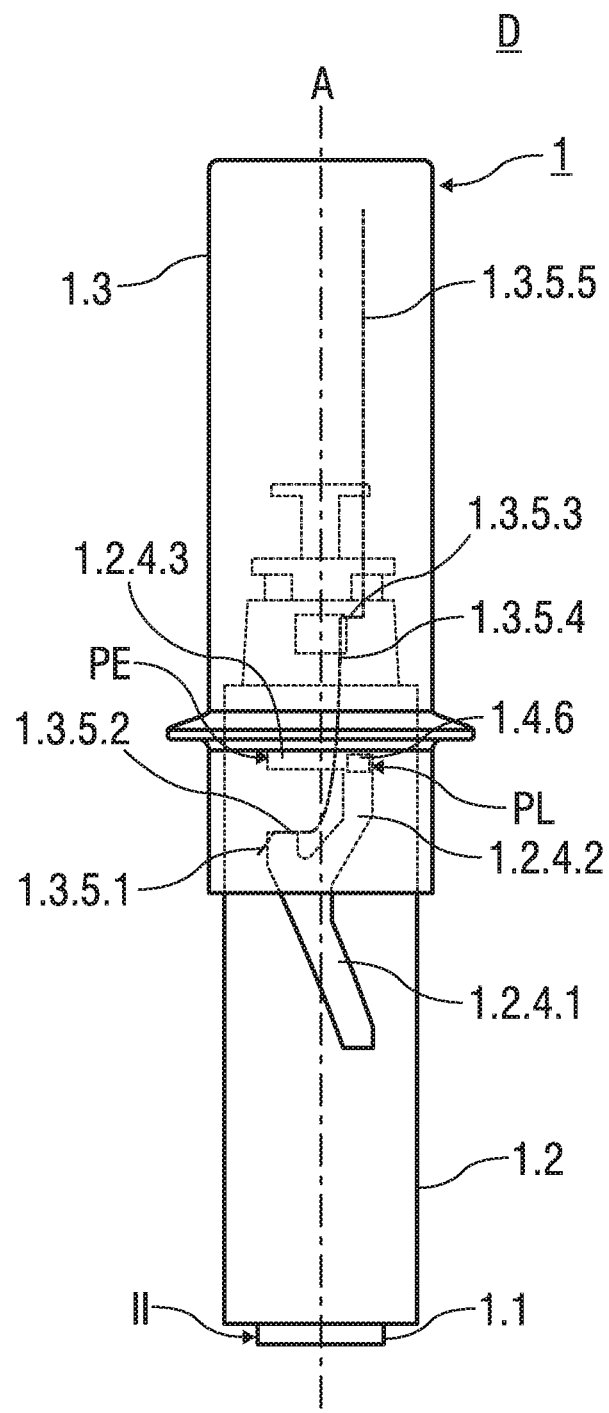
FIG. 15 schematically shows a side view of an injection device with a pre-filled syringe retracted in a support body indicating a location of a guide pin in a lockout position within a guide track and relative to a guide rail.

FIGS. 13 to 15 schematically illustrate a side view of the injection device D, whereas for illustrative purposes the inner guide rail 1.3.5 comprising the inclined, the first lateral, the second lateral and the first axial sections 1.3.5.1, 1.3.5.2, 1.3.5.3, 1.3.5.4 and the second axial section 1.3.5.5, the guide track 1.2.4 comprising first and second paths 1.2.4.1, 1.2.4.2 and the guide pin 1.4.6 normally at least partially hidden from view are shown. The second axial section 1.3.5.5 proximally extends from the second lateral section 1.3.5.3 parallel to the central axis A.

FIG. 13 shows the start position PS of the guide pin 1.4.6 within the guide track 1.2.4 at the beginning of the injection.

During the injection the guide pin 1.4.6 abuts first the first lateral section 1.3.5.2, distally travels within the first path 1.2.4.1 and is laterally deflected, so that it leaves the first lateral section 1.3.5.2 of the guide rail 1.3.5.

FIG. 14 shows the intermediate position PI when the guide pin 1.4.6 reaches a distal end of the first path 1.2.4.1 and abuts a second lateral section 1.3.5.3 of the guide rail 1.3.5. The compression spring 1.5 exerts a biasing force in a proximal direction.

FIG. 15 illustrates the proximal travel of guide pin 1.4.6 by the action of the relaxing compression spring 1.5. The first axial section 1.3.5.4 prevents the guide pin 1.4.6 to return to its start position PS and guides the guide pin 1.4.6 to enter the second path 1.2.4.2 until it reaches a lockout position PL and the pre-filled syringe 2 is retracted within the support body 1.2 and the outer body 1.3.

A further proximal displacement of the outer body 1.3 along the central axis A allows the guide pin 1.4.6, that is biased towards an end position PE by the deflected flexible arm 1.4.5, to enter the end position PE.

Upon reaching the end position PE, the safety device 1 is prevented from re-usage, as a further distal movement of the outer body 1.3 is blocked by the guide pin 1.4.6 abutting the first lateral section 1.3.5.2 and a lateral end section 1.2.4.3 of the second path 1.2.4.2. The lateral end section 1.2.4.3 of the second path 1.2.4.2 extends perpendicular to the central axis A.

The safety device 1 presented herein above has a low number of parts preferably made from a plastics material. The support body 1.2, the outer body 1.3 and the needle sleeve 1.1 comprise the square or alternatively, a rectangular cross-section, so that a relative rotation of these parts 1.1, 1.2, 1.3 is prevented. The design of the safety device 1 significantly differs from standard pre-filled syringes and safety devices for pre-filled syringes. The injection is carried out by a single movement of the outer body 1.3 towards the skin of a patient, whereby the release and retraction mechanism providing needle safety is automatically activated. The safety device 1 comprises a movable release collar 1.4 that slides within the support body 1.2 to release and retract the pre-filled syringe 2 at the end of the injection.

The invention claimed is:

1. A safety device for a pre-filled syringe, comprising
a hollow support body
a release collar non-rotatably arranged within and movable relative to the support body, wherein
a guide track is formed into at least one substantially planar side wall of the support body,
the release collar comprises at least one flexible arm with a guide pin extending from the flexible arm and protruding through the guide track,
the guide pin is movable within and along the guide track in a plane defined by the substantially planar side wall,
wherein the hollow support body has a releaseable mounting means adapted to clamp to a barrel collar of a pre-filled syringe for mounting the pre-filled syringe within the support body, wherein the safety device further comprises:
a hollow outer body slidably arranged with respect to the support body and adapted to receive the support body, wherein the release collar is adapted to release the mounting means,
a guide rail formed into at least one substantially planar inner surface of the outer body and
the guide rail is adapted to abut against the guide pin to guide the movement of the guide pin along the guide track when the outer body is slid relative to the support body.

2. A safety device according to claim 1, characterized in that the flexible arm is deflectable, whereby the deflected flexible arm biases the guide pin in a lateral direction perpendicular to a central axis towards one lateral side of the safety device.

3. A safety device according to claim 2, characterized in that the guide rail comprises a step profile with a plurality of sections that extend substantially parallel to the lateral direction and/or extend substantially parallel to the central axis and/or are oriented with respect to the central axis at an acute angle.

4. A safety device according to claim 1, characterized in that the flexible arm extends essentially parallel to the central axis or is oriented relative to the central axis at an acute angle.

5. A safety device according to claim 1, characterized in that the flexible arm has an arc-shaped and undulated profile.

6. A safety device according to claim 1, characterized in that the flexible arm is connected to the release collar via a hinge and the release collar further comprises a bearing surface that limits a pivoting movement of the flexible arm in the lateral direction.

7. A safety device according to claim 1, characterized in that the flexible arm is connected to or integrally formed to a distal and/or a proximal end of the release collar.

8. A safety device according to claim 1, characterized in that the guide pin is located approximately halfway between a distal end of the flexible arm and the proximal end of the flexible arm.

9. A safety device according to claim 1, characterized in that the guide track comprises a substantially straight first path that is oriented relative to the central axis at an acute angle and a double angled second path with at least three sections, wherein adjacent sections are oriented at an angle with respect each other.

10. A safety device according to claim 1, characterized in that the guide pin is movable within the guide track from a start position to an intermediate position and further to a lockout position, wherein the flexible arm is deflected and stressed when the guide pin is in the lockout position and the guide pin is moved from the lockout position to the end position by the action of the relaxing deflected flexible arm.

11. A safety device according to claim 1, characterized in that a needle shield is retained within and slidable relative to the support body, wherein a compression spring is arranged within the support body that bears against the needle shield in the distal direction and the release collar in the proximal direction.

12. A safety device according to claim 11, characterized in that the needle shield comprises an opening part of resilient plastics material concentrically arranged around a central opening of the needle shield.

13. A safety device according to claim 11, characterized in that the needle shield, the support body and/or the outer body comprise a square or a rectangular cross-section.

14. A safety device according to claim 1, characterized in that the release collar is movable in a proximal direction by the action of the relaxing compression spring, whereby the release collar releases the mounting means of the support body.

15. An injection device comprising a safety device according to claim 1 and a pre-filled syringe.

* * * * *